United States Patent [19]

Guigan

[11] Patent Number: 4,874,114

[45] Date of Patent: Oct. 17, 1989

[54] DEVICE FOR DISPENSING A PREDETERMINED QUANTITY OF A LIQUID

[76] Inventor: Jean Guigan, 9, rue Jean Mermoz, 75008 Paris, France

[21] Appl. No.: 269,349

[22] Filed: Nov. 10, 1988

[30] Foreign Application Priority Data

Nov. 13, 1987 [FR] France .................................. 8715688

[51] Int. Cl.⁴ .............................................. B67D 5/64
[52] U.S. Cl. .................................... 222/168; 222/169; 222/357; 73/864.02; 141/34
[58] Field of Search ............... 222/160, 167, 168, 169, 222/170, 172, 164, 187, 333, 335, 410, 356, 357, 358; 73/864, 864.01, 864.02; 141/34

[56] References Cited

U.S. PATENT DOCUMENTS 2,834,517 5/1958 Townsley .............................. 222/168
3,077,780 2/1963 Takatsky ............................ 73/425.4
3,095,722 7/1963 Fox ....................................... 222/168
3,252,331 5/1966 Lancaster ........................... 73/425.4

FOREIGN PATENT DOCUMENTS 1457933 12/1964 France .

Primary Examiner—Joseph J. Rolla
Assistant Examiner—Kenneth Noland
Attorney, Agent, or Firm—Sughrue, Mion, Zinn, Macpeak & Seas

[57] ABSTRACT

A device for dispensing a predetermined quantity of a liquid comprises: a pipette (1) constituted by a rod having a substantially spherical open element at its end, the element having a calibrated internal volume; mechanical device for holding this pipette either in a first position (51) for filling and for calibration purposes, or else in a second position (52) for emptying purposes; and mechanical device for rotating the pipette at high speed.

5 Claims, 3 Drawing Sheets

DEVICE FOR DISPENSING A PREDETERMINED QUANTITY OF A LIQUID

The present invention relates to a device for dispensing a predetermined quantity of a liquid.

BACKGROUND OF THE INVENTION

In order to perform laboratory analyses, it is often necessary to have a receptacle containing a predetermined quantity of a liquid substance such as a serum or a reagent. This is often achieved by means of a graduated pipette which is used to suck up a certain quantity of liquid; thereafter, the predetermined quantity of liquid is allowed to flow out under gravity.

When the quantity to be dispensed is very small, this method suffers from being inaccurate. In the past, it has not been possible to measure quantities of less than 100 micrometers to within a few percent.

The object of the present invention is to provide a device enabling much smaller quantities, e.g. 5 microliters to 10 microliters, to be dispensed to within 1%, thereby reducing the quantities of serum or reagent required for performing analyses.

SUMMARY OF THE INVENTION

The present invention provides a device for dispensing a predetermined quantity of a liquid, the device comprising:

a pipette constituted by a rod having a substantially spherical element fixed at one end thereof, said element comprising a hollow hemisphere closed by a diametrical partition, thereby defining a volume corresponding to said predetermined dose, a portion of spherical cap extending from said hemisphere to form a liquid inlet chamber which is wide open, said chamber including a peripheral opening leading to the outside and an opening through said partition and putting it into communication with said calibrated volume, said two openings being at a distance from the center of said hemisphere;

mechanical means for holding the free end of said rod in such a manner that the pipette is either in a first position for filling and for calibration purposes, or else in a second position for emptying purposes, said two positions correponding to said diametrical partition being tilted symmetrically in two different directions relative to a vertical plane; and means for rotating said pipette at high speed about a vertical axis both in said first position and in said second position, with the hemisphere being further from the axis of rotation than said inlet chamber when in said first position, and closer in said second position.

In one embodiment, said mechanical means for holding the free end of the pipette are constituted by a support having a plane top portion against which one or other of two push rods come into abutment, with at least one of the push rods being controllable in position, thereby enabling said support to be tilted about a horizontal axis.

The speed of rotation about said vertical axis is such as to obtain a centrifugal force which is sufficient for a liquid of given viscosity.

Said substantially spherical element is made of metal or of plastic material.

Said volume corresponding to said predetermined quantity is about 5 microliters to about 10 microliters.

BRIEF DESCRIPTION OF THE DRAWINGS

An embodiment of the invention is described by way of example with reference to the accompanying drawings, in which.

MORE DETAILED DESCRIPTION

Figure 1:
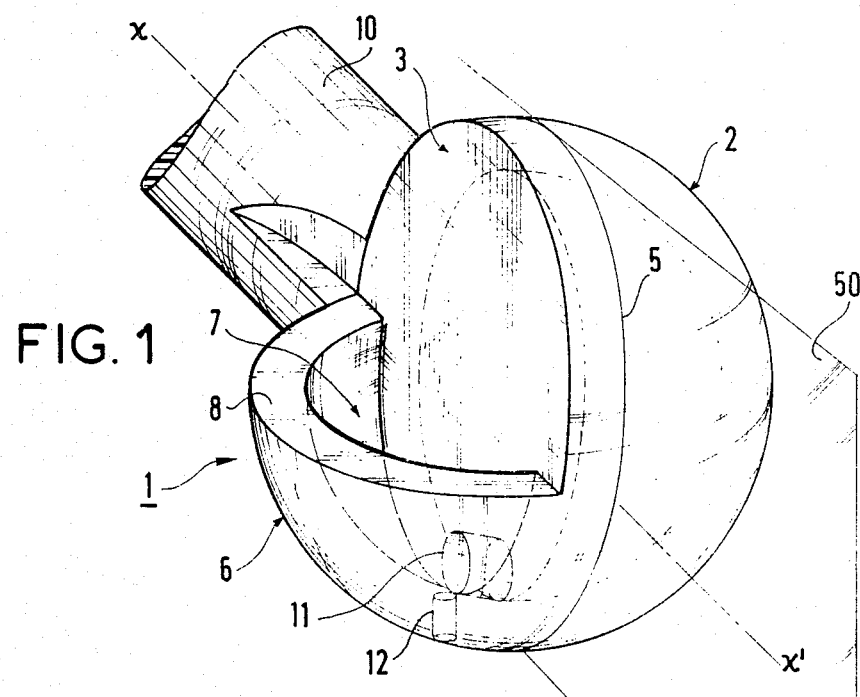
FIG. 1 is a perspective view of the end of a pipette in accordance with the invention.
Figure 2:
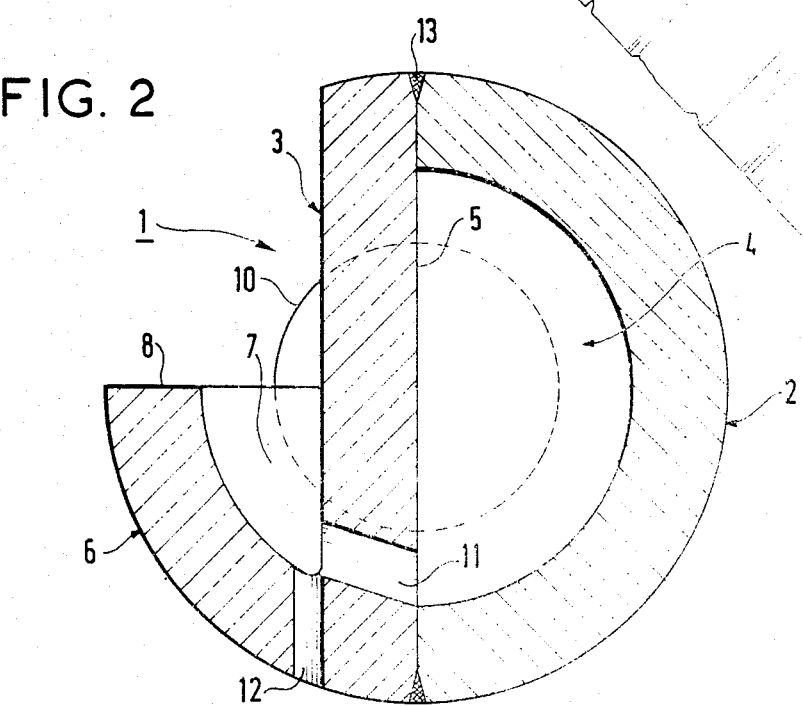
FIG. 2 is a cross-section through the center of the pipette's sphere and perpendicular to the axis xx' of FIG. 1.

FIGS. 1 and 2 show the end of a pipette 1 in accordance with the invention. Its overall shape is that of a sphere from which about one quarter has been rmoved. More precisely, it comprises a hollow hemisphere 2 closed by a diametrical partition 3 thus defining a calibrated inside volume 4. The inside face 5 of the partition 3 is situated in the diametrical plane of the hemisphere 2, but if it is desired to provide an inside volume which is greater than or less than the volume 4, said face may be offset to a small extent relative to said diametrical plane. A hollow portion of spherical cap 6 defines a receiving chamber 7 for the liquid to be calibrated. It is adjacent to the partition 3 and is widely open at its face 8. In addition it has two small openings. A first opening 11 is visible in the plane of FIG. 2 which is a diametrical plane of symmetry through the end of the pipette 1, orthogonal to the axis xx' of FIG. 1. This first opening is preferably situated as far as possible from the center of the sphere and puts the volume 4 and the receiving chamber 7 into communication with each other. A second opening 12 is also visible in the plane of FIG. 2 and is at a distance from the axis of the sphere, serving to put the receiving chamber 7 into communication with the outside.

The pipette in accordance with the invention also includes a rod 10 disposed coaxially with the axis xx' and fixed, as can be seen in the figure, to a portion of the outside face of the hemisphere 2 and to a portion of the outside face of the portion of spherical cap 6.

By way of example, the pipette may be machined from metal such as stainless steel, or else it may be molded from plastic.

When the pipette is made of metal, its end may be built up from two parts: the hollow hemisphere 2; and the partition 3 together with the portion 6 of spherical cap; with these two parts then being fixed together in the zone referenced 13 by laser welding, or by any other equivalent method.

By way of example, the following dimensions may be used:

radius of the sphere (2, 6): 1.683 mm;

thickness of the walls of the sphere (2, 6) and of the diametrical partition 3: 1.7 mm;

diameter of the first opening 11: 0.4 mm; and diameter of the second opening 12: 0.2 mm.

In order to be able to define the position of the FIG. 1 pipette 1 easily relative to its support, it is referenced by means of the plane 50 including the face 5 and the axis xx'. If the axis xx' is vertical, then this plane 50 is seen edge-on in FIG. 3 since it is disposed orthogonally to the plane of FIG. 3.

The pipette 1 can occupy two symmetrical positions relative to the plane 50. A first position 51 for filling and calibration purposes, and a second position 52 for emptying purposes. These two positions are obtained by tilting about an axis 54 contained in the plane 50, with tilting being in the direction of an arrow 53 and being obtained by means described in greater detail below.

Figure 3:
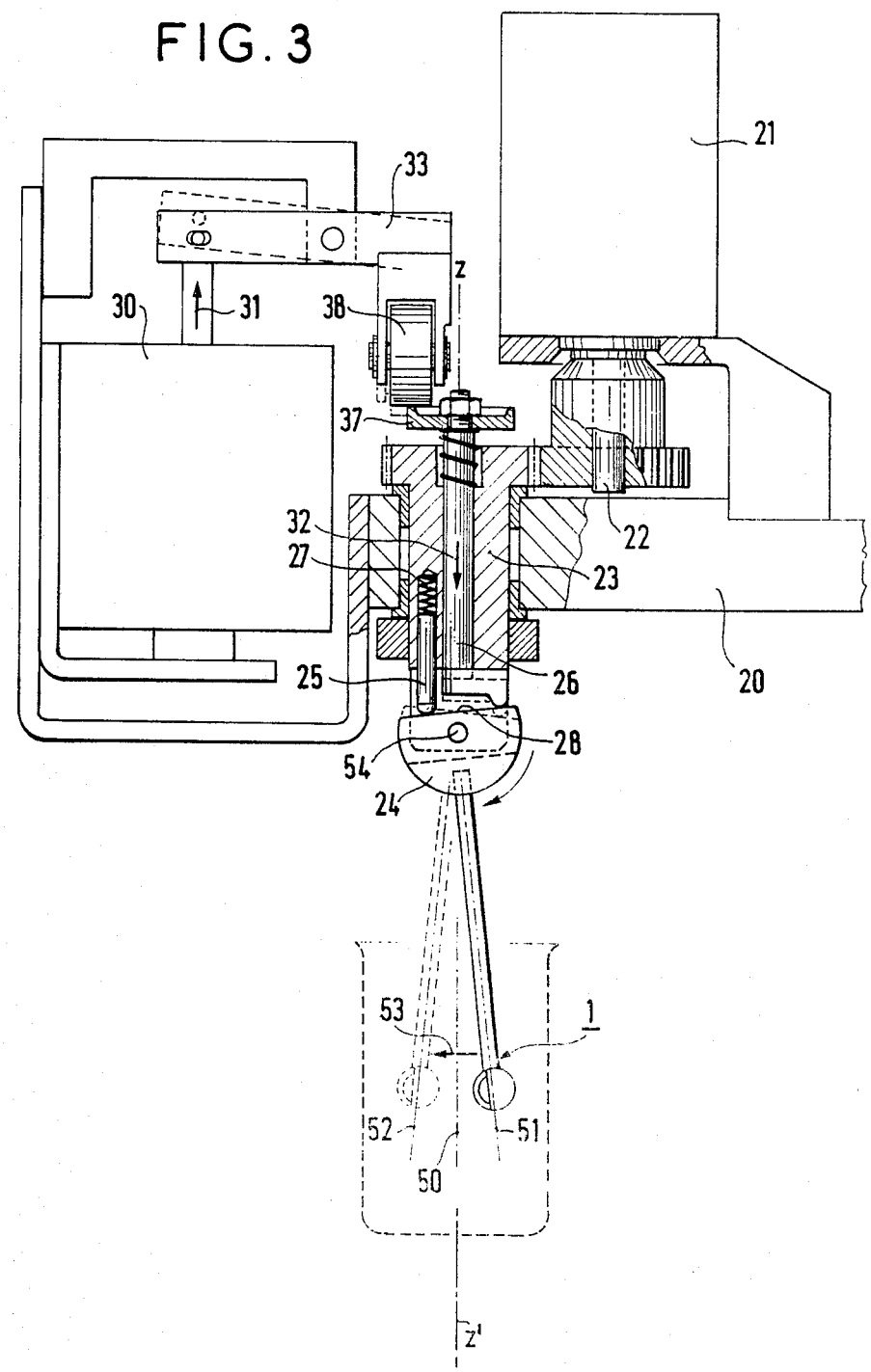
FIG. 3 is a diagrammatic elevation view in partial section of the assembly constituted by the pipette and its mounting.

The mechanical device associated with the pipette and shown diagrammatically in FIG. 3 comprises a fixed frame 20 carrying a fixed motor 21 having a shaft 22 for rotating a block 23 about a vertical axis zz' lying in the plane 50 of FIG. 3, when vertical. The bottom portion of this block is fixed to the support 24 of the pipette 1 which has a plane top face 28 in contact with two push rods 25 and 26. The push rod 25 is received in the block 23 and is urged permanently against the face 28 by means of a spring 27. It holds the pipette in its position 51 as shown by solid lines.

The push rod 26 is capable of taking up a different vertical position under drive from an electromagnetic 30 in the direction of arrow 31, which rocks an arm 33 to drive the push rod in the direction of arrow 32, thereby tilting the support 24 about the axis 54 and moving the pipette to its position 52 which is shown in dashed lines.

The assembly comprising the block 23 and its push rods 25 and 26 rotates about the axis zz'. Contact is maintained between the push rod 26 and the rocker arm 33 by means of a crown wheel 37 co-operating with a roller 38.

By way of example, rotation about the axis zz' may take place at 7,000 revolutions per minute (rpm). The angle between the plane 50 when vertical and when in either of its positions 51 and 52 is about 3°.

Figure 4:
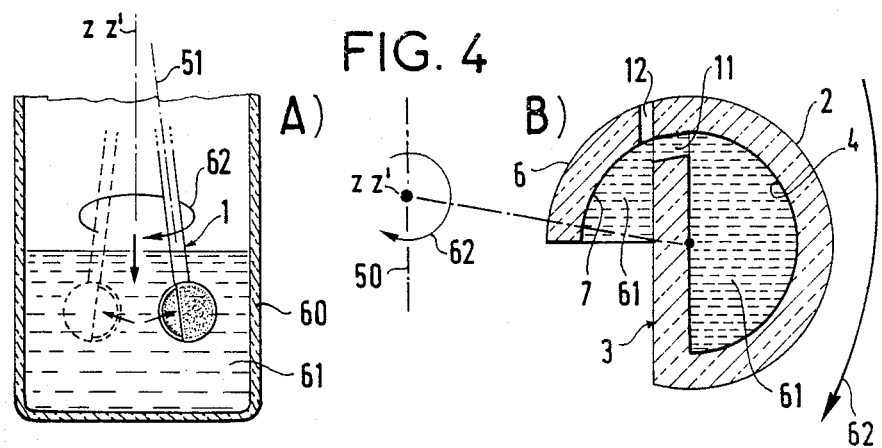
FIGS. 4A and 4B are diagrams showing the pipette filling stage.

The device in accordance with the invention operates as follows: in FIGS. 4A and 4B, FIG. 4A is a diagram showing a receptacle 60 containing a liquid 61 into which the end of the pipette 1 is plunged while in its position 51 of FIG. 3. It is rotated clockwise about the axis zz' as represented diagrammatically by arrow 62. By virtue of the very large centrifugal force acting on the liquid 61, the liquid penetrates into the chamber 7 and fills the inside volume 4 by passing through the opening 11 (see FIG. 4B). It can be seen that the chamber 7 serves to direct the liquid 61 towards the said opening while avoiding turbulence in front of the opening and setting up a pressure rise which facilitates injecting the liquid into the volume 4. It should be observed that no additional opening is required for evacuating air.

Figure 5:
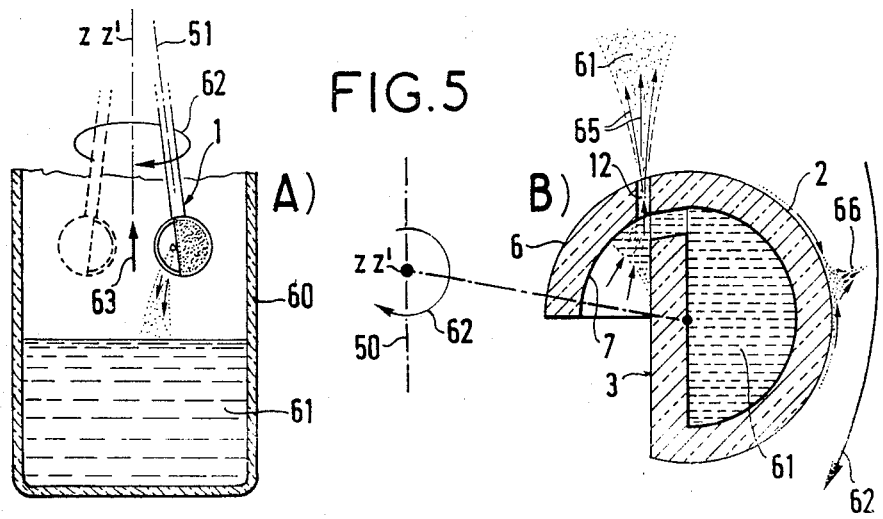
FIGS. 5A and 5B are diagrams showing the pipette calibration stage.

In the stage illustrated in FIGS. 5A and 5B, the pipette 1 is withdrawn from the liquid 61 (arrow 63) while continuing to be rotated in the direction 62 about the axis zz'. As a result, the liquid 61 remaining in the chamber 7 is evacuated by the orifice 12 (arrow 65) and miniscule droplets 66 adherring to the outside surface of the pipette 1 are also evacuated. As a result, the pipette isolates liquid 61 in the calibrated volume 4. This is the calibration stage.

Figure 6:
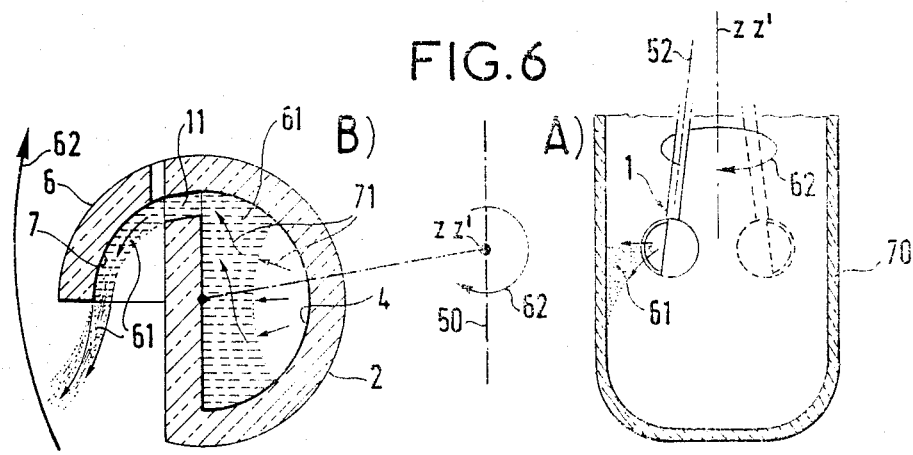
FIGS. 6A and 6B are diagrams showing the pipette emptying stage.

In FIGS. 6A and 6B, the pipette is disposed over a receptacle 70 for receiving the liquid 61. The pipette is now in its second position referenced 52 in FIG. 3 and it is again rotated at high speed about the axis zz', in the same direction 62 as for the preceding operation. This causes the volume 4 to be emptied via the opening 11 and the chamber 7 (arrows 71).

By way of example, the speed of rotation about the axis zz' is 7,000 rpm. Naturally this speed needs to be adapted to the viscosity of the liquid in question.

The means described for tilting the pipette between its two positions 51 and 52 may naturally be replaced by equivalent means.

I claim:

1. A device for dispensing a predetermined quantity of a liquid, the device comprising:

a pipette constituted by a rod having a substantially spherical element fixed at one end thereof, said element comprising a hollow hemisphere partially closed by a diametrical partition, thereby defining a volume corresponding to said predetermined quantity, a portion of spherical cap extending from said hemisphere to form a liquid inlet chamber which is wide open, said chamber including a peripheral opening leading to the outside and an opening through said partition and putting it into communication with said volume, said two openings being at a distance from the center of said hemisphere;

mechanical means for holding the free end of said rod in such a manner that the pipette is either in a first position for filling and for calibration purposes, or else in a second position for emptying purposes, said two positions corresponding to said diametrical partition being tilted symmetrically in two different directions relative to a vertical plane; and means for rotating said pipette at high speed about a vertical axis both in said first position and in said second position, with the hemisphere being further from the axis of rotation than said inlet chamber when in said first position, and closer in said second position.

2. A device according to claim 1, wherein said mechanical means for holding the free end of the pipette are constituted by a support having a plane top portion against which one or other of two push rods come into abutment, with at least one of the push rods being controllable in position, thereby enabling said support to be tilted about a horizontal axis.

3. A device according to claim 1, wherein the speed of rotation about said vertical axis is such as to obtain a centrifugal force which is sufficient for a liquid of given viscosity.

4. A device according to claim 1, wherein said substantially spherical element is made of metal or of plastic material.

5. A device according to claim 1, wherein said volume corresponding to said predetermined quantity is about 5 microliters to about 10 microliters.

* * * * *